[19] United States Patent
Benes

[11] 3,961,038
[45] June 1, 1976

[54] PROCESS FOR THE MANUFACTURE OF INJECTABLE PREPARATIONS OF TC99M AND/OR IN113M AND APPARATUS FOR CARRYING OUT THE PROCESS

[75] Inventor: Ivan Benes, Greifensee, Switzerland
[73] Assignee: Solco Basel AG, Basel, Switzerland
[22] Filed: May 7, 1973
[21] Appl. No.: 357,701

[30] Foreign Application Priority Data
May 8, 1972 Switzerland.......................... 6881/72
Feb. 8, 1973 Switzerland.......................... 1810/73

[52] U.S. Cl................................ 424/1; 252/301.1 R
[51] Int. Cl.$^2$......................................... A61K 43/00
[58] Field of Search................. 424/1; 252/301.1 R

[56] References Cited
OTHER PUBLICATIONS

Chemical Abstracts, vol. 68, No. 20, May 13, 1968, p. 8684, item No. 89869q.
Chemical Abstracts, vol. 73, No. 11, Sept. 14, 1970, p. 65, item No. 52939q.
Nuclear Science Abstracts, vol. 28, No. 11, Dec. 15, 1973, p. 2588, Item No. 27102.
Nuclear Science Abstracts, vol. 27, No. 8, Apr. 30, 1973, p. 1612, Item No. 17158.
Nuclear Science Abstracts, vol. 28, No. 8, Oct. 31, 1973, p. 1704, Item No. 18057.
Nuclear Science Abstracts, vol. 29, No. 11, June 15, 1974, pp. 2580–2581, Item No. 26717 and pp. 2632–2633, Item No. 27157.

*Primary Examiner*—Leland A. Sebastian
*Assistant Examiner*—Christine M. Nucker
*Attorney, Agent, or Firm*—Wenderoth, Lind & Ponack

[57] ABSTRACT

Process for preparing injectable technetium-99m or indium-113m preparation of high specific activity by contacting an aqueous solution of such radionuclide of low specific activity with a metal hydroxide precipitate, separating the precipitate with the radionuclide concentrated therein and dissolving the precipitate in an aqueous solution of a chelating agent.

14 Claims, No Drawings

PROCESS FOR THE MANUFACTURE OF INJECTABLE PREPARATIONS OF TC99M AND/OR IN113M AND APPARATUS FOR CARRYING OUT THE PROCESS

Radionuclides are very extensively used in broad fields of the natural sciences, and numerous branches of industry and medicine. In nuclear medicine, some chemical compounds of short-lived radionuclides are used as diagnostic agents for the detection and diagnosis of various illnesses and organic changes and anomalies. Only short-lived radionuclides are employed for this purpose so that the patient is not subjected to γ-rays longer than is necessary for the investigation. In particular, technetium-99m (Tc99m) and indium-113m (In113m; m = metastable) are used.

In nuclear medicine, Tc99m is used in various forms. Thus, pertechnetate-Tc99m is used, for example, for thyroid diagnosis and for the localisation of brain tumours; Tc99m-sulphur colloid is used, for example, for liver, spleen and bone marrow diagnosis; Tc99m complexes with, for example, aminopolycarboxylic acids are used, for example, for kidney diagnosis and the localisation of brain tumours; Tc99m-albumen is used, for example, for depicting blood vessels and for localisation of the placenta; Tc99m-albumen macro-aggregates are used, for example, for lung scintigraphy; and Tc99m-iron-ascorbic acid complex is used, for example, for kidney and brain scintigraphy.

In nuclear medicine, indium chloride-In113m is used for labelling the transferrin in plasma, for depicting blood vessels and for localisation of the placenta; its derivatives, such as In113m complexes, are used for localisation of brain tumours and for kidney diagnosis; In113m-hydroxide microcolloid is used for liver scintigraphy; and In113m-iron hydroxide macro-colloid is used for lung scintigraphy.

Because of their short life (the physical half-life of Tc99m is 6 hours and that of In113m 100 minutes), these isotopes and their compounds must be manufactured near the place of use. The two isotopes mentioned are produced by radioactive decomposition of their mother isotopes, molybdenum Mo99 or tin Sn113. The isolation of the daughter isotopes is in practice carried out with the aid of so-called radionuclide generators, directly at the place where the material is to be used. The mother isotope, for example as sodium molybdate or ammonium molybdate or as tin-IV chloride, is adsorbed in an adsorption column on a suitable carrier material, such as aluminium oxide, zirconium hydroxide or silica gel; the daughter isotope can be eluted by means of a suitable eluant and thus be separated from the mother isotope. In the case of the Mo99/Tc99m generator the daughter isotope Tc99m is eluted, for example, as pertechnetate ($TcO_4^-$) by means of physiological sodium chloride solution. In the case of the Sn113/In113m generator, the daughter isotope In113m is eluted, for example, as $InCl_3$ with dilute hydrochloric acid.

As already mentioned, Tc99m is obtained from the generator in the form of a pertechnetate which however has a relatively long dwell time in human organs and because of this excessively long "biological half-life" is considered to be unsuitable for most diagnostic applications. Hence, derivatives which are more rapidly excreted by the organism, namely Tc99m cations, are advantageously used instead. To manufacture these derivatives, the pertechnetate ($TcO_4^-$) is reduced from the 7-valent level to a lower valency level, preferably to 4-valency. The literature lists ascorbic acid, preferably in the presence of iron ions, tin-II chloride, sodium borohydride and others as reducing agents.

Normally, the eluates obtained from the generator and the solutions of derivatives which may subsequently be produced have a relatively low specific activity per volume (in the case of Tc99m < 5 mCi/ml, and in the case of In113m < 3 mCi/ml), though this suffices for static scintigraphy. For dynamic studies, to follow rapid functional sequences and for sequence scintigraphy, it is however necessary to administer a high activity in as small a volume as possible. The detectors used are socalled scintillation cameras in combination with film recording or magnetic tape recording and computer evaluation. The specific activity per volume should be at least 10 to 15 mCi/ml.

The manufacture of preparations which meet these requirements has hitherto been time-consuming and expensive. The following methods have hitherto been proposed:

1. The use of Mo99-Tc99m generators of high activity concentration (300 – 500 mCi). On fractional elution, these generators give, within the first few days, pertechnetate eluates of adequate specific activity per volume, namely 10 – 15 mCi/ml. Since the pertechnetate, because it is excreted relatively slowly, cannot be administered advantageously in a higher activity concentration, it is in most cases further converted into derivatives, in the course of which the specific activity per volume decreases further, due to dilution; furthermore, the generators can only be utilised inadequately for these purposes, while generators giving the requisite high activity concentration are expensive.

2. Extraction of an Mo99/Tc99m solution with methyl ethyl ketone, evaporation of the solvent and dissolving the residue in physiological sodium chloride solution [compare Journal of Nuclear Medicine 11, 386 (1970)]. This method requires much time and high expenditure on apparatus, and well-trained personnel. It entails considerable hazard of radioactive contamination of the personnel, the apparatuses and the working area. Special working areas are required, and again only a pertechnetate is obtained.

3. Eluates of indium have hitherto only been concentrated by evaporation of the solvent. Because of the short life of the In113m isotope, the losses are considerable. Here again, well-trained personnel and specially equipped working areas are required.

A process has now been discovered which permits the manufacture of injectable preparations of Tc99m and/or In113m of high specific activity per volume from an aqueous solution, containing the said radionuclides, of low specific activity per volume.

The process according to the invention is characterised in that the radioactive solution is mixed with a sparingly water-soluble metal hydroxide precipitate and the metal hydroxide precipitate, with the radionuclide concentrated therein, is separated off and is dissolved in a small volume of an aqueous solution of a compund capable of forming a stable and physiologically harmless chelate with the metal, under such conditions that the said chelate is formed.

The concentration of Tc-99 and/or In-113m in the metal hydroxide precipitate can be carried out by mixing a metal hydroxide precipitate, which has already been precipitated, with the solution of low specific activity per volume. Preferably, however, the metal hydroxide precipitate is produced in the solution of low specific activity per volume. Surprisingly, the metal hydroxide precipitate acquires substantially the total activity of the starting solution in a short time (approximate order of magnitude 0.01 to 10 minutes) after contact with the solution. The metal hydroxide precipitate thus serves as a carrier.

It has furthermore been found that the new process ensures practically quantitative recovery of the radioactivity, since the loss in radioactivity in the resulting, injectable preparation can decrease to about 2.5 percent, relative to the activity of the starting solution, and to even less if optimum working conditions are observed.

Suitable metal hydroxides for the process according to the invention are Cr-III hydroxide, Yb-III hydroxide, Co-III hydroxide, Fe-II hydroxide, Fe-III hydroxide, Ca hydroxide, Mg hydroxide and Al hydroxide. The use of iron hydroxide, calcium hydroxide, magnesium hydroxide and aluminium hydroxide precipitates is preferred. The use of an iron hydroxide precipitate with or without addition of a reducing agent is particularly preferred.

In a preferred embodiment of the process according to the invention, the metal hydroxide precipitate, containing radionuclide, which has been separated off is dissolved in a small volume of an aqueous solution of a suitable inorganic and/or organic acid and of a chelating agent. A suitable inorganic acid is, for example, hydrochloric acid and a suitable organic acid is, for example, acetic acid. It is however also possible to use, as the organic acid, an acid which at the same time functions as a chelating agent, for example ascorbic acid, citric acid or lactic acid. Suitable chelating agents are, in particular, aminopolycarboxylic acids, such as ethylenediaminetetraacetic acid (EDTA), nitrilotriacetic acid, diethylenetriaminepentaacetic acid, N-hydroxyethylenediaminetetraacetic acid, 1,2-diaminocyclohexanetetraacetic acid and the appropriate salts of these acids. Examples of further suitable chelating agents are deferoxamine, sodium diethyldithiocarbonate, hydralazine, methisazone, 8-hydroxyquinoline, $\beta$-mercaptovaline, N-acetyl-$\beta$-mercaptovaline, 5-amino-1-phenyl-1H-tetrazole, isonicotinic acid hydrazide, 2,3-dimercapto-1-propanol, glycerine, glucose and other compounds, such as have been published in the journal Scientific American, May 1966, pages 40 to 50.

Chelating agents which form, with the metal ions of the hydroxide precipitates used, stable chelates which are harmless to the human body and which are very largely excreted relatively rapidly by the body (for example by glomerular filtration) are preferred.

Particularly preferred chelating agents are ethylenediaminetetraacetic acid, diethylenetriaminopentaacetic acid and their salts.

For example, a Tc99m pertechnetate solution (for example directly from the eluate of an Mo99/Tc99m generator) or an In113m-InCl$_3$ solution (for example directly from the eluate of an Sn113/In113m generator) is used as the starting material and is mixed with a water-soluble salt of a metal of which the hydroxide is sparingly soluble in water at a pH between 2 and 12 and which forms stable and toxicologically harmless chelates, which are preferably excreted by glomerular filtration, with chelating agents, or is mixed directly with the corresponding metal hydroxide. Water-soluble iron-II or iron-III salts, for example iron-II sulphate or iron-II chloride, are particularly suitable as such water-soluble salts. Thereafter, the pH value is displaced into the alkaline region, in the absence or presence of a reducing agent (for example ascorbic acid, tin-II chloride and others), by adding an aqueous alkaline solution such as sodium hydroxide solution, and the corresponding metal hydroxide, for example an Fe-II/Fe-III mixed hydroxide, is thus precipitated. It is also possible to add the Tc99m pertechnetate solution or In113m-InCl$_3$ solution directly to the moist or dry metal hydroxide suspension, in the absence or presence of a reducing agent. The precipitate or the metal hydroxide suspension can be separated off, for example by centrifuging or filtration, a short time after precipitation or after mixing with the metal hydroxide suspension. The precipitate is then preferably dissolved in a little dilute acid, such as hydrochloric acid, the metal ion, for example the iron ion, is masked with a chelating agent, such as ethylenediaminetetraacetic acid, and the solution is brought into an injectable form by addition of suitable buffers, such as a citrate, citrate/phosphate or tris(hydroxymethyl)-aminomethane buffer solution, and by sterilisation. It is preferred to start from solutions which are already sterile or from metal hydroxide suspensions which are already sterile and to work continuously under sterile conditions.

The advantages of the process according to the invention, as compared to the state of the art, lie in the following points:

1. Preparations of high specific activity per volume can be obtained, without great expense, from eluates of low specific activity per volume.

2. Generators can be utilised more economically, even after several half-lives of the mother isotope.

3. By direct processing of solutions of high specific activity per volume, obtained according to the invention, even derivatives such as the abovementioned compounds of Tc99m and In113m used in nuclear medicine can be produced with a high specific activity per volume.

4. The process of the invention does not require specially trained personnel; it can be carried out as a routine procedure.

5. The equipment of a generally customary nuclear-medical laboratory suffices for carrying out the process; special working areas and apparatuses are not required.

6. The solutions of high specific activity per volume which are obtained make it possible to achieve, without difficulties, a bolus effect, which shows good sequence scintigraphs, in application in nuclear medicine.

7. The solutions of high specific activity per volume which are obtained lend themselves well to use as starting solutions for labelling various substances, whereby a higher yield is achievable.

Though the performance of the process does not require special apparatuses, the process can be carried out substantially more simply, rapidly and elegantly with an apparatus developed for it.

The entire manufacture of the ready-to-inject radiopharmacological agent of high activity concentration, is thus preferably carried out in a specially constructed centrifuge tube. The lower terminal portion of this centrifuge tube is of conical shape and serves to receive the radioactive precipitate. The upper part is surrounded by a collar made of glass, which serves for the attachment of a metal cap. The centrifuge tube is closed with a rubber plug protected by the metal cap.

A further subject of the invention is thus an apparatus for carrying out the process comprising:

I. In sterile ampoules, carpoules or disposable syringes
 a. a sterile aqueous solution of compound compund of the metal which forms a sparingly water-soluble hydroxide precipitate,
 b. a sterile aqueous alkaline solution for precipitating the metal hydroxide from the solution according to a), or instead of the solutions under a) and b), the ready metal hydroxide precipitate in the centrifuge tube, and
 c. a sterile aqueous solution of a compound capable of forming a stable and physiologically harmless chelate with the metal, these solutions being in the form of small volumes, and II. a sterile centrifuge tube which is closed by a cap which can be perforated by a canula.

Preferably, the solution according to c) contains an inorganic and/or organic acid and a chelating agent. Additionally to the solution under c), or in this solution, the apparatus can also contain a buffer system.

For example, the apparatus can comprise the following components, the solutions or substances being sterile in each case:
 a. 15 mg of lyophilised iron-II hydroxide in the centrifuge tube;
 b. 0.2 ml of 2 N hydrochloric acid or 0.3 ml of an aqueous solution containing 5 mg of ascorbic acid;
 c. 0.3 ml of 1 M trisodium citrate buffer solution or tris(hydroxymethyl)-aminomethane buffer solution, or
 c. 0.3 ml of 1 M ethylenediaminetetraacetic acid solution or diethylenetriaminepentaacetic acid solution in the form of the sodium salt or calcium salt.

The method of carrying out the process is illustrated by the examples which follows.

EXAMPLE 1

0.6 ml of an aqueous $FeSO_4$ solution (20 mg of $FeSO_4 \cdot 7H_2O$/ml in 0.1 N HCl), followed by 0.6 ml of 1 N NaOH are introduced into 10–15 ml of eluate from an Mo99-Tc99m generator which contains 50 mCi of Tc99m. After thorough mixing, the mixture is left to stand for 1–4 minutes and the resulting precipitate is centriguged off. The precipitate contains more than 96% of the initial activity.

The precipitate is dissolved in 0.2 ml of 2 N HCl, with gentle warming, and 0.25 ml of 0.2 molar EDTA solution is added. The pH value is adjusted to 5–6 with 1 molar citrate buffer. About 0.25 ml is required. After sterilisation, the preparation is ready for administration.

EXAMPLE 2

10 ml of the eluate from a sterile Mo99-Tc99m generator (for example 30 mCi), 0.6 ml of a sterile $FeSO_4$ solution (20 ml of $FeSO_4 \cdot 7H_2O$/ml in 0.1 N HCl) and 0.6 ml of sterile 1 N NaOH are introduced, under sterile conditions, into a sterile centrifuge tube having a rubber cap closure. After mixing, and standing for 1–4 minutes, the resulting precipitate is centrifuged off and the supernatant solution is removed, under sterile conditions, by means of a syringe. The precipitate contains at least 96.5 percent of the initial activity and is dissolved in 0.2 ml of sterile 2 N HCl with gentle warming. Thereafter, 0.25 ml of sterile mixed solution of 1 M EDTA-tetrasodium salt in 1 N NaOH and 1 M citrate buffer, in the ratio of 1:1, is added and the whole is mixed. The preparation is ready to be injected.

EXAMPLE 3

An iron hydroxide precipitate is precipitated out accoridng to Example 2, and separated off; a sterile solution of 20 mg of ascorbic acid in 0.2 ml of $H_2O$ is then added to the precipitate, the mixture is dissolved while warming gently and thereafter 0.25 ml of sterile citrate buffer is added. The Tc99m-Fe ascorbate complex is then ready to be injected.

EXAMPLE 4

An iron hydroxide precipitate is precipitated out and separated off in accordance with Example 2; a sterile solution of 20 mg of citric acid in 0.2 ml of $H_2O$, 0.25 ml of a sterile $SnCl_2$ solution (2 mg of Sn in 1 ml of 0.1 N HCl) and 0.2 ml of citrate buffer is then added to the precipitate. This preparation is ready to be injected. The Tc99m citrate complex serves, for example, to mark the blood vessels.

EXAMPLE 5

10-15 ml of eluate containing 20 mCi from a sterile Sn113/In113m generator, which contains In113m as $InCl_3$, are introduced into a small sterile centrifuge tube having a rubber cap seal, and 0.3 ml of a sterile $FeCl_3$ solution (2.5 mg of $FeCl_3 \cdot 6H_2O$/ml in 0.1 N HCl) and 0.3 ml of a sterile 1 N NaOH (solution) are added. After shaking, the mixture is left to stand for 1–4 minutes and the resulting precipitate is centrifuged off. The supernatant liquid is withdrawn under sterile conditions. It contains less than 2 percent of the initial activity. The precipitate is dissolved in 0.15 ml of sterile 0.1 N HCl and 0.25 ml of a sterile 0.1 molar EDTA solution and 0.3 ml of sterile citrate buffer are added. This makes the In113m preparation ready for injection.

EXAMPLE 6

0.6 ml of a sterile $FeSO_4$ solution (20 mg of $FeSO_4 \cdot 7H_2O$/l ml of 0.1 N HCl) and 0.6 ml of sterile 1 N NaOH are introduced, under sterile conditions, into a sterile centrifuge tube having a conical bottom. After mixing, the solvent (water) is removed from the resulting precipitate, under a nitrogen atmosphere, by lyophilic drying (freeze-drying). 10 ml of the Tc99m eluate (20 mCi) are added under sterile conditions to the precipitate thus obtained, in the centrifuge tube. After mixing, and standing for 4 minutes, the suspension is centrifuged off and the supernatant solution is removed by suction filtration under sterile conditions. The precipitate contains at least 95 percent of the initial activity and is dissolved in 0.2 ml of sterile 2 N HCl, while warming gently. Thereafter, 0.25 ml of a sterile solution which consists of 1 M ethylenediaminetetraacetic acid tetrasodium salt in 1 N NaOH and 1 M citrate buffer, in the ratio of 1:1, is added and the whole is mixed. The preparation is ready for injection; it contains an activity of just 20 mCi.

EXAMPLE 7

An iron hydroxide precipitate is precipitated out, and separated off, analogously to Example 6. 0.4 ml of a sterile solution which consists of 4 percent strength citric acid solution and 0.1 N sodium hydroxide solution in the ratio of 1:1 is then added to the precipitate and the whole is mixed. The preparation is ready for injection.

EXAMPLE 8

An iron hydroxide precipitate is precipitated out and separated off analogously to Example 6. The precipitate is then dissolved in 0.2 ml of 2 N HCl while warming gently. Thereafter, 0.3 ml of a sterile solution which consists of 0.5 M ethylenediaminetetraacetic acid tetrasodium salt and 2 M tris(hydroxymethyl)-aminomethane, in the ratio of 1:2, is added and the whole is mixed. The preparation is read for injection.

EXAMPLE 9

15 ml of the eluate from a sterile Tc99m generator (15 mCi) and 0.3 ml of a sterile mixed solution of $FeSO_4$ (20 mg $FeSO_4.7H_2O$/ml) and $SnCl_2$ (1 mg $Sn^{++}$/1 ml) in 0.2 N HCl are introduced under sterile conditions into a sterile centrifuge tube having a rubber cap closure. Thereafter, 0.6 ml of sterile 1 N NaOH are also added. After mixing, and standing for 4 minutes, the resulting precipitate is centrifuged off and the supernatant solution is removed. The precipitate contains 98.5 percent of the initial activity and is dissolved in 0.2 ml of sterile 2 N HCl whilst warming gently. Thereafter, 0.3 ml of a sterile solution which consists of 0.5 M ethylenediaminetetraacetic acid tetrasodium salt and 2 M tris-(hydroxymethyl)-aminomethane in the ratio of 1:2 is added and the whole is mixed. The preparation does not contain any free Tc99m pertechnetate and is ready for injection; it contains an activity of about 15 mCi.

I claim:

1. Process for preparing an injectable preparation of a radionuclide selected from the group consisting of technetium-99m and indium-113m of high specific activity per volume, which comprises contacting an aqueous solution of the radionuclide of low specific activity per volume with a sparingly water-soluble metal hydroxide precipitate, separating the metal hydroxide precipitate, with the radionuclide concentrated therein, from the aqueous solution, and dissolving said metal hydroxide precipitate in an aqueous solution containing a dissolved compound capable of forming a stable and physiologically acceptable chelate with the metal ions of the metal hydroxide to form a chelate of the metal.

2. Process according to claim 1, wherein the metal hydroxide precipitate is produced in the solution of low specific activity per volume by adding a water-soluble salt of the metal to the solution and adding an aqueous alkaline solution to the resultant solution in an amount sufficient to cause precipitation of the metal hydroxide.

3. Process according to claim 1, wherein the solution of low specific activity is mixed directly with the metal hydroxide precipitate which has been previously prepared.

4. Process according to claim 1, wherein the metal hydroxide precipitate is an iron hydroxide, calcium hydroxide, magnesium hydroxide or aluminum hydroxide precipitate.

5. Process according to claim 1, wherein the separated metal hydroxide precipitate is dissolved in an aqueous solution of the chelating agent and at least one acid selected from the group consisting of inorganic and organic acids.

6. Process according to claim 5, wherein the organic acid is a chelating agent.

7. Process according to claim 6, wherein the organic acid is ascorbic acid, citric acid or lactic acid.

8. Process according to claim 5, wherein the acid is hydrochloric acid or acetic acid.

9. Process according to claim 5, wherein the chelating agent is an aminopolycarboxylic acid or a salt thereof.

10. Process according to claim 9, wherein the chelating agent is the ethylenediaminetetraacetic acid, diethylenetriaminepentaacetic acid or a salt thereof.

11. Process according to claim 1, wherein the solution containing the separated metal hydroxide precipitate is mixed with an aqueous buffer system solution.

12. Process according to claim 11, wherein the buffer system solution is a citrate, mixed citrate-phosphate or tris (hydroxymethyl) aminoethane buffer solution.

13. Process according to claim 11, wherein a mixed solution of the chelating agent and the buffer is used for the chelate formation.

14. Process according to claim 1, wherein the starting materials and solutions are sterile and the process is carried out under sterile conditions throughout.

* * * * *